United States Patent
Breininger et al.

(10) Patent No.: US 11,490,964 B2
(45) Date of Patent: Nov. 8, 2022

(54) PLANNING SUPPORT FOR AN INTERVENTIONAL PROCEDURE

(71) Applicant: Siemens Healthcare GmbH, Erlangen (DE)

(72) Inventors: Katharina Breininger, Erlangen (DE); Marcus Pfister, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 364 days.

(21) Appl. No.: 16/708,706

(22) Filed: Dec. 10, 2019

(65) Prior Publication Data
US 2020/0188024 A1     Jun. 18, 2020

(30) Foreign Application Priority Data

Dec. 14, 2018 (EP) ..................... 18212612

(51) Int. Cl.
| | | |
|---|---|---|
| *A61B 34/10* | (2016.01) | |
| *G06T 19/20* | (2011.01) | |
| *G16H 30/40* | (2018.01) | |
| *G16H 50/50* | (2018.01) | |
| *A61B 90/00* | (2016.01) | |

(Continued)

(52) U.S. Cl.
CPC ............ *A61B 34/10* (2016.02); *A61B 90/361* (2016.02); *A61B 90/92* (2016.02); *G06T 7/10* (2017.01);
(Continued)

(58) Field of Classification Search
CPC ........ A61B 2034/101; A61B 2034/104; A61B 2034/105; A61B 2034/107; A61B 2090/364; A61B 2090/367; A61B 34/10; A61B 90/361; A61B 90/92; G06T 19/20; G06T 2207/30101; G06T 2210/41;
(Continued)

(56) References Cited

U.S. PATENT DOCUMENTS

| | | | | |
|---|---|---|---|---|
| 2009/0306948 | A1* | 12/2009 | Irving ..................... | G06T 13/20 703/6 |
| 2016/0262914 | A1* | 9/2016 | Raaz ......................... | A61F 2/82 |

(Continued)

FOREIGN PATENT DOCUMENTS

| | | |
|---|---|---|
| DE | 102016212882 A1 | 1/2018 |
| WO | WO2017007947 A1 | 1/2017 |

OTHER PUBLICATIONS

NEJMvideo, Youtube video: NEJM Procedure: Deployment of an Endovascular Graft in an Abdominal Aortic Aneurysm, Nov. 12, 2009. https://www.youtube.com/watch?v=qUpXJBoAoWI (Year: 2009).*

(Continued)

*Primary Examiner* — Sing-Wai Wu
(74) *Attorney, Agent, or Firm* — Lempia Summerfield Katz LLC

(57) ABSTRACT

The disclosure relates to a method and also to a correspondingly configured imaging device for planning support for an interventional procedure. In the method, a model of a hollow organ is created from a 3D image dataset. A deformation of the hollow organ is then simulated based on a course of a guide facility in the hollow organ through a deformation of the model. In accordance with the deformed model, a spatially resolved compression and/or stretching of the hollow organ, which is brought about by an introduction of the guide facility, is determined and specified.

16 Claims, 5 Drawing Sheets

(51) Int. Cl.
  *A61B 90/92* (2016.01)
  *G06T 7/10* (2017.01)
  *G06T 17/20* (2006.01)

(52) U.S. Cl.
  CPC .............. *G06T 17/20* (2013.01); *G06T 19/20* (2013.01); *G16H 30/40* (2018.01); *G16H 50/50* (2018.01); *A61B 2034/104* (2016.02); *A61B 2034/105* (2016.02); *A61B 2034/107* (2016.02); *A61B 2090/364* (2016.02); *A61B 2090/367* (2016.02); *G06T 2207/30052* (2013.01); *G06T 2207/30101* (2013.01); *G06T 2210/41* (2013.01); *G06T 2219/2012* (2013.01); *G06T 2219/2021* (2013.01)

(58) Field of Classification Search
  CPC .... G06T 2219/2012; G06T 2219/2021; G16H 30/40; G16H 50/50
  See application file for complete search history.

(56) References Cited

U.S. PATENT DOCUMENTS

| | | |
|---|---|---|
| 2017/0027683 A1 | 2/2017 | Douthitt |
| 2018/0014884 A1 | 1/2018 | Kowarschik |

OTHER PUBLICATIONS

Watermark, Youtube video: Abdominal Aortic Graft—Medical Animation by Watermark, Jan. 2, 2013. https://www.youtube.com/watch?v=QEvBHAEKKcQ (Year: 2013).*

European Search Report for European Patent Application No. 18212612.8-1122 dated Jun. 5, 2019.

Koutouzi, Giasemi. "Three-dimensional guidance for Endovascular Aortic Repair" Department of RadiologyInstitute of Clinical Sciences. 2017. pp. 1-87.

Roy, David, et al. "Finite element analysis of abdominal aortic aneurysms: geometrical and structural reconstruction with application of an anisotropic material model." The IMA Journal of Applied Mathematics 79.5 (2014): 1011-1026.

Toth, Daniel, et al. "Adaption of 3D models to 2D x-ray images during endovascular abdominal aneurysm repair." International Conference on Medical Image Computing and Computer-Assisted Intervention. Springer, Cham, 2015. pp. 1-8.

Pfister, Marcus. "Determination and consideration of calcifications in the visualization and deformation of segmentation meshes" Prior Art Journal, vol. #06, pp. 37-39, 2016 // ISBN: 978-3-945188-34-7 with machine translation.

* cited by examiner

PLANNING SUPPORT FOR AN INTERVENTIONAL PROCEDURE

The present patent document claims the benefit of European Patent Application No. 18212612.8, filed Dec. 14, 2018, which is hereby incorporated by reference.

TECHNICAL FIELD

The disclosure relates to a method and an imaging device for planning support for an interventional procedure, to a corresponding computer program, and to a storage medium with a computer program of this type.

BACKGROUND

With the progress that is being made nowadays in medical technology, in particular in data acquisition and imaging and also data processing, new opportunities are being produced for supporting a doctor or a surgeon. Such support by technical and thus objective means and means that do not depend on the performance on the day for example may contribute to improved treatment and thus ultimately to the wellbeing of the patient, because the respective doctor undertaking the treatment obtains more and/or new information by comparison with conventional methods for example and/or may be relieved of the load of acts or activities that previously had to be carried out manually.

A method for planning support for an interventional procedure is already known from German Patent Application DE 10 2016 212 882 A1, for example. In this method, a three-dimensional image dataset of a hollow organ is provided and segmented. The three-dimensional image dataset then has a two-dimensional image of a guide facility superimposed on it. Subsequently, a corrected position of a section of the hollow organ is determined. Based on this corrected position, a deformation energy of the hollow organ in the section may then be determined for a removal of the guide facility.

SUMMARY AND DESCRIPTION

The object of the present disclosure is to give technical assistance, which makes it possible without any complications for a doctor to carry out an interventional procedure for placing an auxiliary element in a hollow organ.

The scope of the present disclosure is defined solely by the appended claims and is not affected to any degree by the statements within this summary. The present embodiments may obviate one or more of the drawbacks or limitations in the related art.

The method is embodied for planning support for an interventional procedure for placing an auxiliary element in a hollow organ by a guide facility that is stiffer than the hollow organ. The auxiliary element may be a stent for a blood vessel or—in neuroradiology for example—an intracranial stent, but likewise a valve or the like, for example. The guide facility may be or may include a wire, a probe, a gripper, an endoscope, and/or more besides. The fact that the guide facility is stiffer, (e.g., may be bent or deformed less easily than the hollow organ), means that when the guide device is introduced into or guided into the hollow organ or is present in the hollow organ, the hollow organ may deform, e.g., may adapt itself to the guide facility. As part of the present method, a 3D image dataset is acquired, which maps an uninfluenced course of the hollow organ. This uninfluenced course of the hollow organ thus corresponds to its arrangement and shape without the guide facility.

The 3D-image dataset is then segmented, wherein a model, e.g., a virtual geometrical object or a virtual representation of the hollow organ in its uninfluenced course or state for example, is created. The 3D dataset may be a three-dimensional computed tomography image (CT image), a CT angiography image, a magnetic resonance image (MR image, MRT image) or the like, e.g., recorded pre-operatively such as before the interventional procedure.

As a further part of the present method, a deformation of the hollow organ is then simulated on the basis of a course of the guide facility in the hollow organ by a deformation of the model of the hollow organ. It is thus considered here how the guide facility—actually or estimated or assumed—will run or is likely to run in the hollow organ. The course of the guide facility may then be predetermined or initially determined. In the simulation or the deformation of the model, this may be made to cover the same area as the predetermined or determined course of the guide facility. If the hollow organ is a blood vessel, for example, then its model may be deformed in such a way that the guide device or a representation or a model of the guide facility, in accordance with the simulation, e.g., in accordance with the deformed model of the hollow organ, is located in the vessel, e.g., is surrounded by the hollow organ.

Depending on the way in which or the method by which the 3D image dataset has been created or acquired and the course of the guide facility was determined, a registration between the course determined and the 3D dataset, in particular the uninfluenced course of the hollow organ and the model of the hollow organ, may be carried out. Ultimately a consistent relative spatial arrangement or combination of the 3D image dataset, of the course of the guide facility and of the model of the hollow organ may be created or given. Methods and procedures known to the person skilled in the art, for example, a 2D-3D or 3D-3D registration, may be used for an appropriate registration.

A biomechanical model of the hollow organ may be predetermined for the simulation of the deformation. Parameters such as a flexibility or stiffness of the hollow organ may be predetermined as a function of a concrete application case. Corresponding values may be known or may be estimated, for example, from previous measurements and/or simulations. Likewise, for example, an adaptation of the deformation correction may be carried out, to which end for example the publication "Adaption of 3D Models to 2D X-Ray Images during Endovascular Abdominal Aneurysm Repair" by Daniel Toth and Marcus Pfister et al. provides a background. This simulation, e.g., a determination of an—at least assumed—course of the hollow organ may be carried out before the auxiliary element is introduced into the hollow organ.

In accordance with the disclosure, as part of the present method, a spatially resolved compression and/or stretching of the hollow organ in its longitudinal extent direction in its deformed course in accordance with the deformed model compared to the uninfluenced course of the hollow organ is determined and specified automatically. The spatially resolved compression and/or stretching thus specifies an area-by-area change in length of the hollow organ as a result of the deformation caused or brought about by the guide facility—and possibly anatomical peripheral conditions. This change in the length of the hollow organ may not be homogeneous in such cases, for example, as a result of inhomogeneous material characteristics of the hollow organ in different areas, for example, in the form of calcifications, as a result of different diameters in different areas of the hollow organ, as a result of a different nature of the surrounding tissue and/or other similar factors. The specification of the spatially resolved compression and/or stretching may mean or include a corresponding data output, a marking (e.g., a graphical marking) or identification or the like. Thus, for example, areas of the hollow organ may be specified or marked in which the hollow organ is compressed during the deformation, and/or areas of the hollow organ in which the organ will be stretched during the deformation. In addition, or as an alternative, corresponding numerical values and/or spatial specifications, (e.g., coordinate specifications or the like), may be given, (e.g., output or displayed). The present disclosure recognizes here that a specification about the spatially resolved compression and/or stretching is especially useful, because especially strongly compressed or possibly stretched areas, which expand or contract again after the guide facility is removed, e.g., at least deform to approximately assume their original shape in accordance with the uninfluenced course, are ultimately unsuitable or suboptimal as a landing zone for the auxiliary element.

Thus, for example, at least one area of relatively low and/or relatively great compression and/or stretching of the hollow organ—related in each case to an extent determined along the deformed model, for example, a maximum extent, such as a size or intensity of the stretching and/or compression of the hollow organ—may be specified as a suitable or unsuitable landing zone for the auxiliary element.

An actual measured view of the hollow organ may only be available to the doctor carrying out the respective procedure in the form of the pre-operative 3D image dataset or two-dimensional angiographies. On the basis of this 3D dataset or these angiographies with the uninfluenced course of the hollow organ however the doctor may not readily or reliably detect or read off the way in which the hollow organ will deform and how the relative spatial location relationships or distances between different areas of the hollow organ will change or be displaced by the introduction of the guide facility. During the intervention, for example, only the guide facility, but not the hollow organ itself or the organ only as a projection may be recognizable on a fluoroscopy image or an angiography, so that here too no direct starting point for the doctor carrying out the procedure emerges with regard to a deformation behavior of the hollow organ and thus with regard to areas suitable or unsuitable as landing zones.

Areas that are subject to a relatively great change in length, e.g., to a compression and/or stretching, will as a rule move relatively greatly or far after the removal of the guide facility. Were the auxiliary element or a landing zone of the auxiliary element to be located in such an area that changes greatly in length, this may lead to complications after the removal of the guide facility, such as to a displacement or slipping of the auxiliary element. This in its turn may potentially lead to the auxiliary element no longer fulfilling its current task or function and/or for example to vessels branching off from the hollow organ being hidden or covered by the auxiliary element, whereby a blood supply to surrounding tissue or other organs may be adversely affected.

The present disclosure thus advantageously makes it possible to place the auxiliary element in an area specified as a suitable landing zone or accordingly to avoid areas of the hollow organ that are unsuitable as a landing zone. Because this is based on a simulation or modeling process that may be objectively checked, is predetermined and is independent, in this way, for example, any influence of a possible lack of experience of the doctor carrying out the procedure or a restriction during imaging or the like produced in an individual case may be minimized for a successful treatment. Especially advantageously, the present disclosure makes it possible for the respective doctor carrying out the procedure, supported in the specification of the spatially resolved stretching and/or compression, or if necessary the specification based thereon for the suitable or unsuitable landing zones, to arrange the auxiliary element in a safe position. In such cases, it may be possible to dispense with the administration of additional contrast media to make the hollow organ recognizable during the procedure. Thus, stress for the respective patient during the procedure may possibly also be reduced by the present disclosure.

A landing zone is in particular an area in which an end or edge of the auxiliary element is arranged or will be arranged. In these edge areas, a change in length of the hollow organ may have an especially significant effect on a relative position of the auxiliary element in the hollow organ. For example, during the change in length, when the vessel resumes its original shape, a pressure or a force may be exerted on the edge area or the end of the auxiliary element and may move the element. Likewise, the auxiliary element may have an effect on mechanical characteristics of the hollow organ, so that, in the area of the landing zone, a corresponding difference in the mechanical characteristics of the hollow organ exists between an area in which the auxiliary element is located and in an area directly adjoining the landing zone, which is free from the auxiliary element. The result here may then accordingly be an inhomogeneous behavior during the return of the hollow organ to its original shape, whereby the auxiliary element may likewise be displaced.

The spatially resolved compression and/or stretching may be determined absolutely or relatively. Accordingly, for example, at least one threshold value for a maximum change in length, e.g., compression or stretching, of the hollow organ may be predetermined. If this threshold value is exceeded locally, e.g., in a specific area or part area of the hollow organ, then this area may be classified or specified as unsuitable for a landing zone. Similarly, an area in which the threshold value is undershot, e.g., not exceeded, will be classified or specified as suitable for a landing zone. The threshold value in this case may be predetermined as an absolute value. The threshold value may likewise be specified as a relative value, for example, e.g., as a percentage figure related to a maximum change in length occurring along the hollow organ, for example. The threshold value may likewise be dynamically predetermined or adapted depending on the individual case for example.

For example, the case may occur in which, with an actual patient or hollow organ, there is no area without a change in length. The determination or specification of one or more areas of the least or relatively little or the greatest or relatively great change in length may then still make possible a best possible choice of landing zone. For example, all areas, in which the respective local change in length amounts to more than 50% of a maximum value occurring or determined in each case along the hollow organ, may be classified or specified globally as areas of relatively great length change and thus be classified as an unsuitable landing zone. Similarly, areas in which the local change in length amounts, for example, to less than 50% or 25% of the change in length occurring or determined in the individual case in the respective hollow organ may be classified or specified as areas of relatively small length change and thus be classified as a suitable landing zone. Especially advantageously in such cases a continuous or gradual scale may be predetermined or used, on which or in accordance with which the local or area-by-area changes in length are specified. This advantageously makes possible an especially simple and intuitive identification of an area suitable as a landing zone.

In an advantageous embodiment, at least one at least two-dimensional image, e.g., a two-dimensional or three-dimensional image or a corresponding image dataset, which maps the guide facility in the hollow organ, is recorded and superimposed on the 3D image dataset. The at least one at least two-dimensional image, also referred to below for the sake of simplicity as the two-dimensional image or 2D image, may be an x-ray, angiography, or fluoroscopy image recorded for example during the procedure. Likewise, other imaging modalities, for example, ultrasound or the like, might possibly be used. As already mentioned, for consistent superimposition, first of all a registration between the 3D image dataset and the two-dimensional image, e.g., between respective coordinate systems of these images or data or of devices or apparatus used to acquire or record them may be carried out, in particular automatically. The course of the guide facility is then determined from the at least one at least two-dimensional image and/or from the superimposition. In this case a segmentation of the 2D image may be provided or carried out, in order to delimit the guide facility from other parts of the 2D image. In this form of embodiment, the guide facility may thus already be located in the hollow organ. The course of the guide facility determined on the basis of the 2D image is then advantageously the actual real course and is thus especially precise and reliable. As described, the guide facility may be a wire, which is thus then able to be recognized and identified in the 2D image even without contrast medium. Because the guide facility is located by definition or prerequisite in the hollow organ, the course of the guide facility forms a boundary condition for the deformation of the hollow organ and the corresponding simulation or modeling and may accordingly be provided as input or default in a corresponding simulation model or simulation program.

In an advantageous development, an anatomical feature of the hollow organ is identified in the 3D image dataset, which is also visible with an imaging modality used for the at least two-dimensional image and which—at least probably—will be displaced or moved by the introduction of the guide facility into the hollow organ. This may be related for example to an internationally fixed coordinate system. The anatomical feature will then also be identified in the at least two-dimensional image, e.g., recognized or detected. The deformed model is further superimposed on the at least two-dimensional image. Then, to establish an accuracy of the simulation of the deformation, in the superimposition from the at least two-dimensional image and the deformed model, a distance between the anatomical feature from the at least two-dimensional image and the same anatomical feature on the deformed model is determined. The superimposition from the two-dimensional image and the deformed model in this case may be a separate superimposition or be combined or will be combined with the superimposition of the 3D image dataset. In other words, both the two-dimensional image and also the deformed model may thus be superimposed on the 3D image dataset.

Because the two-dimensional image reflects the actual physical reality, it may serve as a reference, in relation to which the deformed model may be evaluated. Provided the simulation, e.g., the deformation of the model of the hollow organ, is correct, e.g., realistic, in the superimposition the anatomical feature on the deformed model will be located precisely where the two-dimensional image also shows this anatomical feature. A distance threshold value may be predetermined, for example. If this distance threshold value is reached or exceeded by the distance determined or exceeded, a corresponding warning may be output. Thus, it will be pointed out by this warning that the accuracy of the simulation or modeling of the deformation is too low, e.g., that the deformed model does not reliably or accurately correspond to reality. In this way, it may advantageously be prevented that the respective doctor carrying out the procedure starts out using false assumptions or preconditions, so that overall a probability of a successful procedure may be improved.

The anatomical feature may be an especially thick area of tissue or a transition between two areas of tissue or types of tissue with different visibility, corresponding to a contrast edge or a sudden change in contrast in the two-dimensional image, a vessel fork, or branch or the like. Such an anatomical feature may advantageously not only—even with a displacement—be identified or localized especially accurately and reliably, but also be visible with an additional administration of contrast media or already with a reduced amount of contrast media, whereby stress on the patient or on the hollow organ may advantageously be kept as low as possible.

In a further advantageous embodiment, to determine the course of the guide facility in the hollow organ this course is estimated based on a position of a predetermined planned insertion point for introduction of the guide facility into the hollow organ relative to a predetermined planned target region for the auxiliary element and based on a predetermined shape and stiffness of the guide facility, in particular automatically, before the guide facility is introduced into the hollow organ. In other words, the method proposed here may thus be carried out entirely pre-operatively. This advantageously makes it possible to carry out the corresponding simulations, modeling, and estimates in an especially detailed manner, because corresponding calculations do not have to be available in real time for example. In this way, for example, the procedure may advantageously be planned even better or with more detail and greater reliability. For example, an especially accurate form and length of the auxiliary element tailored to the respective patient may be selected before the beginning of the actual procedure.

In order to estimate the course of the guide facility global specifications or defaults may be used for example for a type of tissue lying between the insertion point and the target region, for example its stiffness or deformability. Likewise, data available from the 3D dataset or other examinations or measurement data of the respective patient may be taken into account for these, for example. In particular when the stiffness of the guide facility is—very much—greater than the stiffness of the hollow organ and/or of the surrounding tissue, a bending of the guide facility through contact with the hollow organ or through an influence or pressure of the surrounding tissue may possibly be ignored. In the simplest case, it may be possible for example to estimate the course of the guide facility in the hollow organ by the guide facility or a virtual model of the guide facility being superimposed on the 3D dataset and being aligned in accordance with the insertion point and the target region. A planned path along which the guide facility is to be guided from the insertion point to the target region, in order for example to take account in doing so of a planned rotation of the guide facility in the estimation of the course of the guide facility, may be advantageous.

In a further advantageous embodiment, to create the model of the hollow organ, its surface is emulated by virtual mesh elements. Such mesh elements may be or may include triangles, vertices, connecting edges, and/or points of a point cloud and/or the like. The spatially resolved compression and/or stretching is then determined by determining and comparing a plurality of distances between mesh elements adjacent to one another before and after the deformation. In other words, for pairs of mesh elements corresponding to one another in the undeformed and the deformed model, their respective distance from one another is determined. In such cases a greater compression or stretching is present the smaller or the larger the distance between two mesh elements is in the deformed model by comparison with the distance between the corresponding mesh elements in the undeformed model. In other words, a change in the distance occurring in the modeled or simulated deformation of the model of the hollow organ between given points or mesh elements of the model is evaluated. In such cases, the deformation may leave a principle topology of the model unchanged, as is also the case for a physically real hollow organ. This method makes possible an especially simple determination of the compression and/or stretching and one that is able to be carried out with relatively little computing effort, wherein the spatial resolution is only limited by the resolution or by a degree of detail of the model. The use of adjacent mesh elements in such cases specifies a local deformation. Likewise, however mesh elements that are not directly adjacent may also be used, e.g., the change in the distance between them determined. In this way, a resolution of the changes in length and thus a computing effort needed may be set or adapted.

In a further advantageous embodiment, the compression and/or stretching is determined by a Finite Element Method (FEM) simulation on the model of the hollow organ. This may be carried out before the procedure, wherein then the estimated course of the guide facility and the undeformed model, which thus specifies the uninfluenced course of the hollow organ, may be used or predetermined as input, e.g., as the initial situation and as a boundary condition, for the FEM simulation. The FEM simulation may be used as an alternative or in addition to the other methods described here. If both methods are employed, then this method may be used for verification or plausibility checking of the respective results. The use of an FEM simulation may advantageously deliver especially accurate results. The combinations with the estimated course of the guide facility may be especially advantageous in this case, because there may be no restrictions in respect of the speed of computation, so that an especially accurate and reliable result may be established. FEM simulations are sufficiently well known as a mathematical tool from other areas of application. Further background information on this topic may be taken from the publication "Finite element analysis of abdominal aortic aneurysms: Geometrical and structural reconstruction with application of an anisotropic material model" by David Roy, Gerhard A. Holzapfel, et al. in IMA Journal of Applied Mathematics (2014) 79, 1011-1026, doi: 10:1093/imamat/hxu037, for example.

In a further advantageous embodiment, the simulation of the deformation of the hollow organ is carried out under the boundary condition of a minimal expenditure of energy (e.g., for the registration of the undeformed model with the course of the guide facility). Basically, starting from the uninfluenced course, there may be a number of options as to how and in what way the hollow organ deforms as a reaction to the guide facility being introduced, e.g., may adapt itself to the course of the guide facility. As recognized by the present disclosure, through the boundary condition or default that the deformation may take place with a minimal expenditure of energy and/or that the hollow organ in its deformed shape may exhibit a minimal energy or mechanical stress consistent with a non-destructive deformation, a realistic and physiologically plausible result may be achieved. For example, a number of types of deformation of the deformation paths simulated or modeled of an expenditure of energy needed in each case or a resulting energy of an end state may be compared, wherein that type of deformation and/or that end state that exhibits the lowest energy or the lowest expenditure of energy may be selected.

The deformation may likewise be carried out act-by-act, for example, wherein, using each intermediate act or intermediate state as a starting point, a number of possible next deformation acts may be compared with one another in respect of their expenditure of energy needed, wherein that act of the number of possible next intermediate acts that exhibits the lowest expenditure of energy is then selected. In this case, for example, defaults in respect of material characteristics or material parameters of the hollow organ and/or of the surrounding tissue may be specified and used as boundary conditions or defaults for the simulation.

In a further advantageous embodiment, at least one fixed point, in particular the insertion point for introducing the guide facility into the hollow organ and/or for a bifurcation of the hollow organ, is predetermined before the simulation of the deformation, which remains in a fixed position during the simulation of the deformation, for example related to an internationally recognized coordinate system. Specifying such fixed points is especially advantageous in this case because, by doing so, the simulation may be simplified, e.g., a computing effort needed significantly reduced. At the same time, the accuracy of the simulation is not significantly adversely affected, because from experience it may be assumed that the corresponding fixed points actually do not move or only move to a negligible extent.

In a further advantageous embodiment, in particular on the basis of the 3D image dataset, an inhomogeneity is detected which influences a flexibility of the hollow organ area-by-area or locally. For an area of the model of the hollow organ corresponding to the detected inhomogeneity, a higher stiffness value of the model is then specified for the simulation of the deformation compared to a remainder, e.g., other areas. Such an inhomogeneity may be a calcification, for example. By considering such inhomogeneities, the deformation of the hollow organ may be simulated especially realistically. This in its turn may advantageously contribute to the auxiliary element ultimately actually ending in a suitable position, in which it may fulfill its intended function or task. In such case, inhomogeneities may also be taken into consideration that have been detected by other methods or imaging modalities or measurements, whereby the accuracy or realism of the simulation may be further improved.

In a further advantageous embodiment, to specify the spatially resolved compression and/or stretching of the hollow organ, at least one area of relatively less and/or relatively greater compression and/or stretching on the deformed model and a corresponding area on the undeformed model are color-coded in accordance with a predetermined color scale. In other words, areas of relatively great change in length are color coded differently to areas of relatively small change in length in the two models. In this case, a continuous color scale may be used, comparable to a heat map. This advantageously makes possible an especially fast and intuitive acquisition and determination of suitable landing zones. Likewise, respective sizes of the suitable or unsuitable areas may be made especially easy and intuitive to acquire, for example compared to a tabular specification of numerical values. For example, areas of relatively great change in length may be colored or marked in shades of red, areas of medium change in length in shades of yellow and areas of relatively small change in length in shades of green.

In a further advantageous embodiment, a flexibility of the auxiliary element and/or a fixed-position anchoring point of the auxiliary element on the hollow organ is predetermined. Then, an autonomous reformation of the hollow organ with inserted auxiliary element and without the guide facility will be simulated as a function of the spatially resolved stretching and/or compression determined as well as well as of the predetermined flexibility and/or the predetermined anchoring point. Then, on the basis reformation simulation, a likely displacement of the auxiliary element in the hollow organ between its position before and after the reformation, e.g., before and after the removal of the guide facility from the hollow organ, is determined. If it is established in this case that the likely displacement exceeds a predetermined threshold value and/or in accordance with the reformation simulation the auxiliary element or an end of the auxiliary element are likely to end up, e.g., come to rest, in an area unsuitable as a landing zone, an appropriate warning may be output automatically. The auxiliary element ending up or coming to rest in an unsuitable or unintended location or position in the hollow organ after the procedure is ended may advantageously be prevented by this. Likewise, the or a further threshold value, e.g., a maximum permitted displacement, may advantageously be predetermined and used as an additional boundary condition for specifying or determining the area or areas suitable or unsuitable as a landing zone.

For example, the case may occur that, because of the autonomous reformation of the hollow organ, the auxiliary element with introduced guide facility has to be positioned in an area unsuitable per se as a landing zone, so that after the removal of the guide facility and the reformation of the hollow organ occurring, it ends up in an area suitable as a landing zone. Such a procedure would be counterintuitive and not able to be used reliably without the present disclosure.

Taking account of the flexibility and/or of the anchoring point may improve the accuracy of the reformation simulation in this case, because the hollow organ with the inserted auxiliary element might possibly behave differently than without the auxiliary element, e.g., during the deformation on introduction of the guide facility. Especially advantageously a result of the reformation simulation, e.g., a simulated end position of the hollow organ and of the auxiliary element, may likewise be superimposed on the 3D image dataset, in particular before and/or during the procedure. This may advantageously make a dynamic optimization or adaptation of the position or arrangement of the auxiliary element possible for the respective doctor carrying out the procedure, in particular when the reformation simulation is carried out again or updated automatically after an automatically acquired or detected displacement or change in position of the auxiliary element by the doctor carrying out the procedure.

In a further advantageous embodiment, a part area of the hollow organ to be treated, for example to be supported or sealed by the auxiliary element, is predetermined. This part area may thus correspond to the target region already mentioned, in which the auxiliary element is ultimately to be positioned. Depending on the spatially resolved compression and/or stretching, an appropriately adapted or optimized length of the auxiliary element is then automatically proposed. In this case, one or more boundary conditions may be predetermined, wherein the boundary conditions are fulfilled. For example, it may be predetermined as a boundary condition that the part area is completely covered or concealed by the auxiliary element and/or that the auxiliary element ends in the area of relatively low compression and/or stretching and/or at least one anatomical feature, (e.g., a vessel branch), may not be concealed. The length of the auxiliary element, e.g., its size or extent in particular in the longitudinal direction of the hollow organ, may then automatically be varied until such time as all these predetermined boundary conditions are fulfilled.

The boundary conditions may likewise be predetermined with a respective priority or a weight. Then, by automatic variation of the length and checking of a result in respect of the boundary conditions, an optimal length of the auxiliary element may be determined automatically. In this way, an optimal treatment result may be provided regardless of the experience of the doctor carrying out the procedure.

It may be pointed out at this juncture that any surgical acts stated or indicated here for illustration in connection with the method are explicitly not part of the claimed method. The described method is thus only claimed in as much as it does not include any surgical act. However, this does not preclude the method being able to be carried out nor its applicability, because, as described, the method may be carried out entirely preoperatively for example. Even if the method may advantageously be carried out at least partly during the interventional procedure, it merely relates to a controlling of the imaging device or of a data processing device and not to the surgical acts possibly carried out during a procedure.

A further aspect of the present disclosure is an imaging device for planning support for an interventional procedure for placing an auxiliary element in a hollow organ by a guide facility that is stiffer than the hollow organ. The imaging device in this case has an acquisition device for acquiring a 3D image dataset, which maps an uninfluenced course of the hollow organ.

Such an acquisition of the 3D image dataset in the sense of the present disclosure may mean or include a recording or measurement of the 3D image dataset, e.g., of corresponding raw data or measured values. Accordingly, the acquisition device may include an imaging modality, e.g., a radiation source and a corresponding detector or a magnet and coil arrangement or the like. Likewise, the acquisition may also be or mean or include a retrieval of the 3D image dataset from a data memory. The acquisition device may then be a data processing device or part of a data processing device, which acquires, (e.g., retrieves), the 3D image dataset via a corresponding data or communication interface. The same may also apply to an acquisition of the at least one at least two-dimensional image.

The imaging device further has a data processing device coupled to the acquisition device. The recognition device in this case may be or include part of the data processing device, e.g., a corresponding circuit and/or a corresponding program module.

The imaging device is configured to execute or carry out at least one form of embodiment of the method. The imaging device may be the imaging device stated in connection with the method. Accordingly, the imaging device may have individual, a few or all of the characteristics, components and/or embodiments stated in connection with the method.

The acquisition device may likewise be embodied and configured to acquire the at least two-dimensional image. The data processing device may correspondingly be embodied and configured to create the model, to determine the course, to simulate the deformation, to automatically determine, and specify the spatially resolved compression and/or stretching. The data processing device may likewise be embodied and configured to determine and specify at least one area of relatively low and/or relatively great compression and/or stretching as a suitable or unsuitable landing zone for the auxiliary element. The same applies to the features described in connection with the advantageous embodiments and developments of the method.

A further aspect of the present disclosure is a computer program or computer program product, (e.g., program code), including commands which, when the computer program is executed by an imaging device, in particular by the imaging device, cause the device to execute at least one form of embodiment of the method, in particular semi-automatically or fully automatically. The computer program thus encodes or represents the method acts of the method. The commands of the computer program may accordingly be or include control commands or control instructions for the imaging device.

A further aspect of the present disclosure is a computer-readable storage medium, on which at least one form of embodiment of the computer program is stored.

To carry out the method, the imaging device, in particular its data processing device, may have a computer-readable storage medium as well as a processor device connected thereto, for example a microprocessor or microchip or microcontroller. This processor device is then embodied and configured to execute the computer program stored on the computer-readable storage medium.

A further aspect of the present disclosure is a data medium signal, which the computer program transmits.

The characteristics and developments of the method and of the imaging system specified here and below as well as the corresponding advantages are able to be transferred mutually in each case by analogy between these and likewise to the other aspects of the disclosure, e.g., to the computer program and the computer-readable storage medium, and vice versa. Thus, such developments of the imaging device, of the method, of the computer program, and of the computer-readable storage medium, which have embodiments that, to avoid unnecessary redundancy, are not explicitly described separately in the respective combination or for each of these aspects, also belong to the disclosure.

BRIEF DESCRIPTION OF THE DRAWINGS

Further features, details and advantages of the present disclosure emerge from the description of exemplary embodiments given below and also with reference to the drawings. In the drawings.

DETAILED DESCRIPTION

Figure 1:
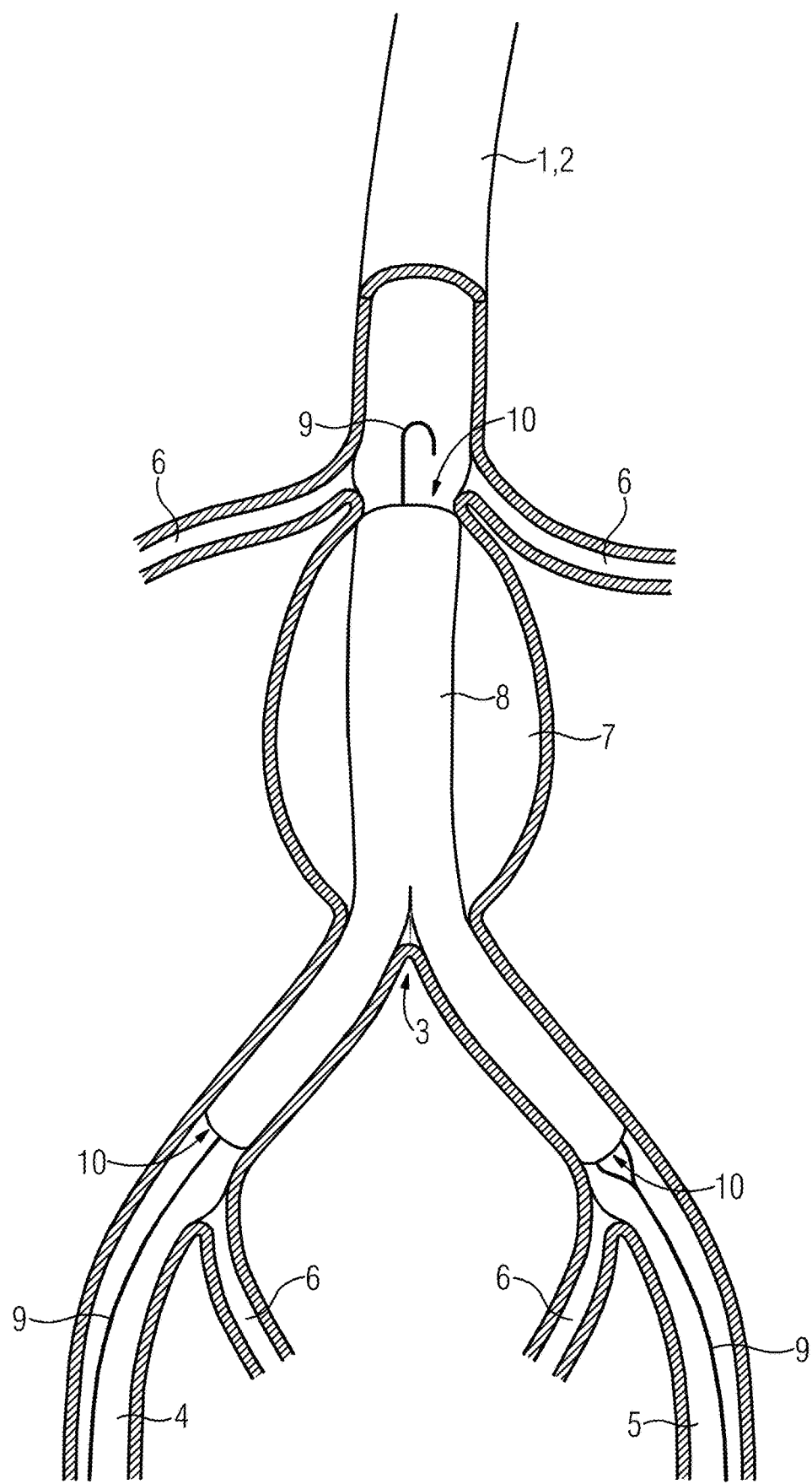
FIG. 1 depicts a schematic diagram of an example of a section of a hollow organ with an auxiliary element inserted therein.

The exemplary embodiments of the disclosure are provided herein. In the exemplary embodiments, the components of the forms of embodiment described each represent individual features of the disclosure to be considered independently of one another, which also each develop the disclosure independently of one another and are thus to be seen individually or in a combination other than that shown as a component of the disclosure. Furthermore, the forms of embodiment described are also able to be supplemented by further of the features of the disclosure already described.

In the figures, for the sake of clarity, the same elements, elements having the same functions or elements corresponding to one another are labeled with the same reference characters in each case, even if this may involve different instances or examples of the corresponding elements.

FIG. 1 depicts a schematic, part cutaway view of a hollow organ 1. The hollow organ 1 here may include the common iliac artery 2 (Arteria iliaca communis) for example and the internal iliac artery 4 (Arteria iliaca interna) and external iliac artery 5 (Arteria iliaca externa) branching off at a bifurcation 3 of this. Also shown are sectional views of a few further vessels 6 branching off. The hollow organ 1 in the present example has a diseased vascular aneurysm 7, which in the present example may also involve an abdominal aorta aneurysm. Such vascular aneurysms 7 may be treated by insertion of a stent 8. The stent 8 may be positioned by a guide facility 9, which may involve a wire for example, in the hollow organ 1 in the area of the vascular aneurysm 7. In order to avoid a retrograde filling of the vascular aneurysm 7, the stent 8 may be extended via the bifurcation 3 into the branching-off iliac arteries 4, 5. End areas of the stent 8 or areas or sections of the hollow organ 1 in which the stent 8 ends are also referred to as landing zones 10. It is necessary for treatment of the vascular aneurysm 7 for the stent 8 to be positioned in the area of the vascular aneurysm 7. It has turned out however that the exact location or positioning of the landing zones 10 may have a significant influence on the long-term success of the treatment of the vascular aneurysm 7.

Figure 2:
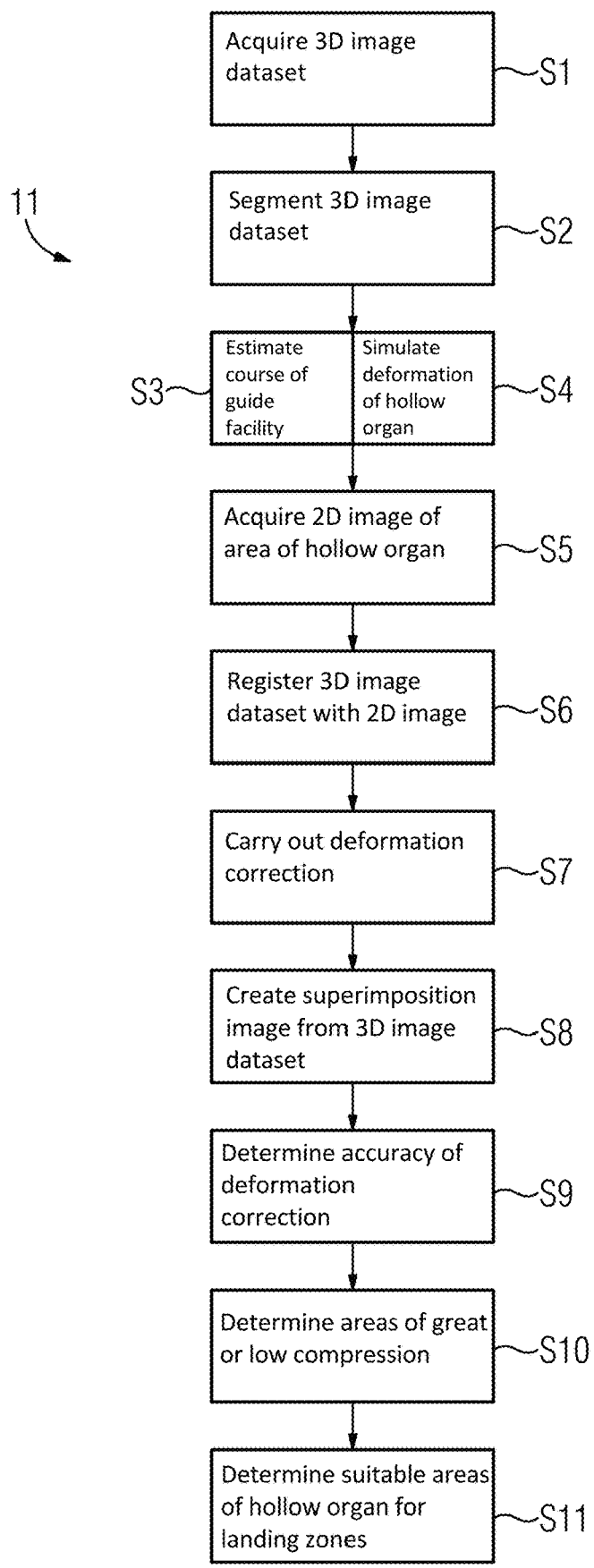
FIG. 2 depicts an example of a schematic flowchart for a method for planning support for an interventional procedure for placing the auxiliary element in the hollow organ by a stiff guide facility.

FIG. 2 depicts a schematic flowchart 11 for a method for planning support for an interventional procedure for placing an auxiliary element, (for example, the stent 8), in the hollow organ 1 by the guide facility 9 stiff in relation to the hollow organ 1. This method will be explained in greater detail below with reference to the remaining figures.

Figure 3:
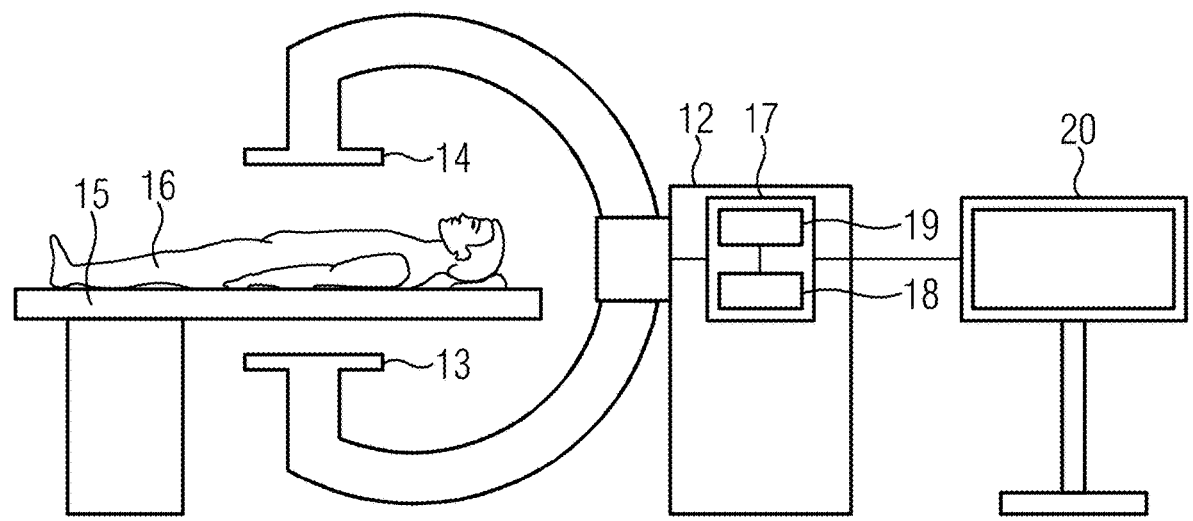
FIG. 3 depicts a schematic diagram of an example of an imaging device for carrying out the method.

FIG. 3 depicts a schematic diagram of an example of an imaging device 12 for carrying out this method. The imaging device 12 in the present example includes a C-arm x-ray device with a radiation source 13 and a detector 14 arranged opposite the source. Arranged between the radiation source 13 and the detector 14 is a patient couch 15, on which in the present example a patient 16 to be imaged, to be examined or to be treated is located. In the present example the imaging device 12 further has a data processing device 17 with a computer-readable storage medium 18 and a processor device 19 connected thereto. A computer program, which is able to be executed by the processor device 1, and which encodes or represents the method acts of the method for planning support may be stored on the storage medium 18. The method acts of this method may thus be program modules or function blocks of the corresponding computer program.

In the present example, the data processing device 17 is configured to acquire and process image data recorded for example by the radiation source 13 and the detector 14, wherein this may involve a 3D CT image dataset and also for example angiography or fluoroscopy images recorded continuously during the procedure, e.g., radiology images. Also provided here is a display device 20 connected to the data processing device 17 for displaying the image data or corresponding image processing results created by the data processing device 17.

For the procedure to position the stent 8 in the vascular aneurysm 7, the imaging device 12 may thus be used as an angiography system for x-ray fluoroscopy of the patient 16 or of the hollow organ 1 respectively. Initially however, pre- or intraoperatively in a method act S1, a 3D image dataset of an area of the hollow organ 1 is acquired, in this example by the image processing device 17, for example. The 3D image dataset may be recorded by the imaging device 12 itself or may be retrieved from data source provided. The 3D image dataset may be recorded or have been recorded with administration of contrast medium and in the present example shows a major anatomy of the hollow organ 1 and of the vascular aneurysm 7.

In a method act S2, the 3D image dataset is segmented automatically, semi-automatically or manually. In this act, a virtual geometrical model of the hollow organ 1 is created from the 3D image dataset. The advantage of such a model is that it may be processed and worked on computationally, e.g., by the data processing device 17, more elegantly, e.g., more easily and more quickly, than a volume dataset, e.g., than the pure 3D image dataset. The created model may include centerlines of imaged vessels, thus in the present example the iliac arteries 2, 4, 5 and the branching-off vessels 6, for example, as well as mesh elements or surface meshes, which map or emulate a surface of the vessels or of the hollow organ 1, e.g., model it.

It is assumed in the present example that the 3D image dataset and its segmentation has been carried out pre-operatively. Then, in a method act S3, a likely course of the guide facility 9 in the hollow organ 1 is likewise estimated pre-operatively by the data processing device 17. For example, in parallel with this, in a method act S4, on the basis of the created model, an FEM simulation of a deformation of the hollow organ 1 brought about by the introduction of the stiff guide facility 9 into the hollow organ 1 may be carried out pre-operatively, in order to determine a compression and/or stretching of the hollow organ 1 area-by-area, e.g., spatially resolved. The method acts S3 and S4 may be optional.

In a method act S5, an at least two-dimensional image of an area of the hollow organ 1, which shows or maps the guide facility 9 in the hollow organ 1 may be recorded or acquired during the procedure.

Figure 4:
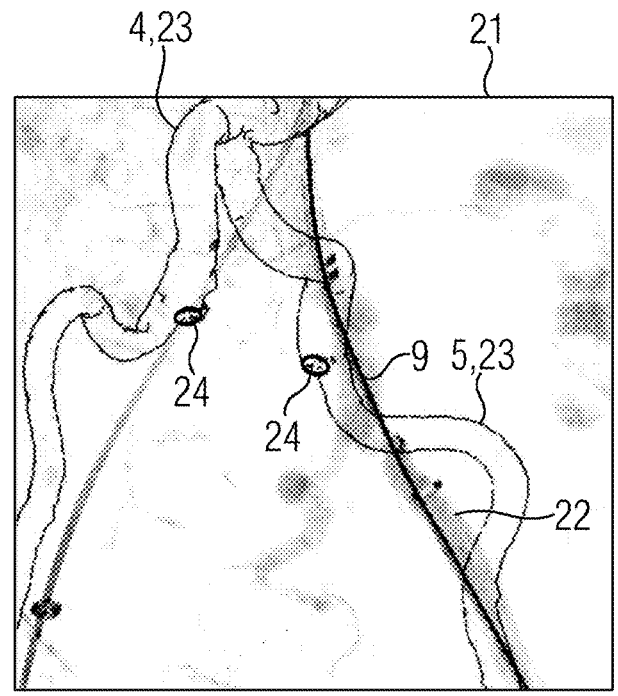
FIG. 4 depicts a schematic superimposition diagram including an example of a model of a hollow organ in an uninfluenced course and an image of the guide facility in the hollow organ.

In a method act S6, a registration between the 3D image dataset and the two-dimensional image, e.g., between corresponding coordinate systems, may be carried out, provided both the 3D dataset and also the two-dimensional image have not been recorded by the same imaging device 12 with an unchanged setting or location of the patient 16. The model of the hollow organ 1 created by the segmentation of the 3D image dataset may then, in method act S6, be superimposed on the two-dimensional image in a consistent, e.g., spatially correct or realistic way. FIG. 4 depicts a schematic diagram of a corresponding 2D superimposition image 21, in which the undeformed model 23 of the hollow organ 1 created from the pre-operative 3D image dataset is superimposed on a two-dimensional subtraction image. The two-dimensional subtraction image here shows a contrast medium shadow 22 of contrast medium, which has been introduced into the hollow organ 1, as well as the guide facility 9 arranged in the hollow organ 1. It may be seen here, that although the guide facility 9 and the contrast medium shadow 22 are consistent with one another in their courses or arrangements, the undeformed model 23 of this is not consistent, however. In accordance with the undeformed model 23, the guide facility 9 would multiply penetrate the hollow organ 1, which is not actually the case, because the guide facility 9 is being guided in the hollow organ 1. In the present example, a few anatomical features 24, which have been established on the basis of the 3D image dataset are marked here on the undeformed model 23. These anatomical features 24 may involve exits of the branch vessels 6 or the like.

Figure 5:
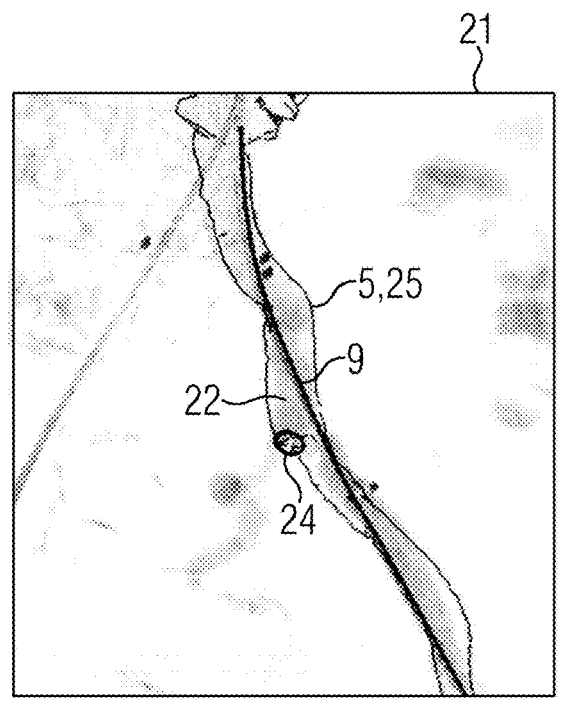
FIG. 5 depicts a schematic superimposition diagram an example of the image from FIG. 4 after deformation and adaptation of the model to a course of the guide facility.

In a method act S7, a deformation correction, e.g., a simulation or modeling of the deformation of the undeformed model 23 may be carried out, by which this is made to cover the same area as the course of the guide facility 9. Thus, to this end the stiff guide facility 9 introduced into the hollow organ 1 is detected manually or automatically and the undeformed model, e.g., the corresponding superimposed segmentation is correspondingly deformed. This occurs in particular before the introduction of the stent 8. FIG. 5 depicts a schematic diagram of the 2D superimposition image 21 from FIG. 4 for this, with the difference that here it is not the undeformed model 23, but a corresponding, deformed model 25 of the hollow organ 1 created that is superimposed. The deformed model 25 or its course is now consistent with the course or the arrangement of the stiff guide facility 9 and the contrast medium shadow 22. The guide facility 9 thus now runs in the deformed model 25. The deformation of the undeformed model 23 to the deformed model 25 may be carried out as a mesh deformation, in which originally mesh elements or mesh elements of the undeformed model 23 are allocated new positions, wherein however a principle topology of the undeformed model 23, e.g., also of the corresponding mesh elements, which emulate or map its surface, remain unchanged. The undeformed model 23 may thus be compressed, stretched or rotated for example, but not divided into a number of parts however and put together again in another way.

The 2D superimposition image 21 shown in FIG. 5 with the deformed model 25 may be created for example in method act S7 or in a subsequent method act SS8. In method act SS8, a superimposition image 26 from the pre-operative 3D image dataset shown schematically in FIG. 6, here, for example, a 3D CT image 27 and the two-dimensional image or the 2D superimposition image 21 and for example the models 23, 25, may be created. For orientation an insertion point 28, in which the guide facility 9 is introduced into the hollow organ 1, the bifurcation 3 and an aorta bifurcation 30 lying above it are indicated. The 3D CT image 27 shows an uninfluenced course 29 of the hollow organ 1, here for example the iliac arteries 4, 5. In the 3D superimposition image 26, however, as may already be seen in FIG. 4, it may be seen that the actual course of the guide facility 9 in the hollow organ 1 is not consistent with the uninfluenced course 29. Instead the hollow organ 1 actually runs along the guide facility 9 that may be seen. It may be seen here that the introduction of the guide facility 9 into the hollow organ 1 has led to a shortening, e.g., to a for example concertina-like compression of the hollow organ 1. The reason for this is at least partly that the insertion point 28 and the aorta bifurcation 30 are not just mobile or able to be moved in any given way, but for example function as fixed-location fixed points, and the guide facility 9 is stiffer, e.g., less easily bendable than the hollow organ 1.

Figure 6:
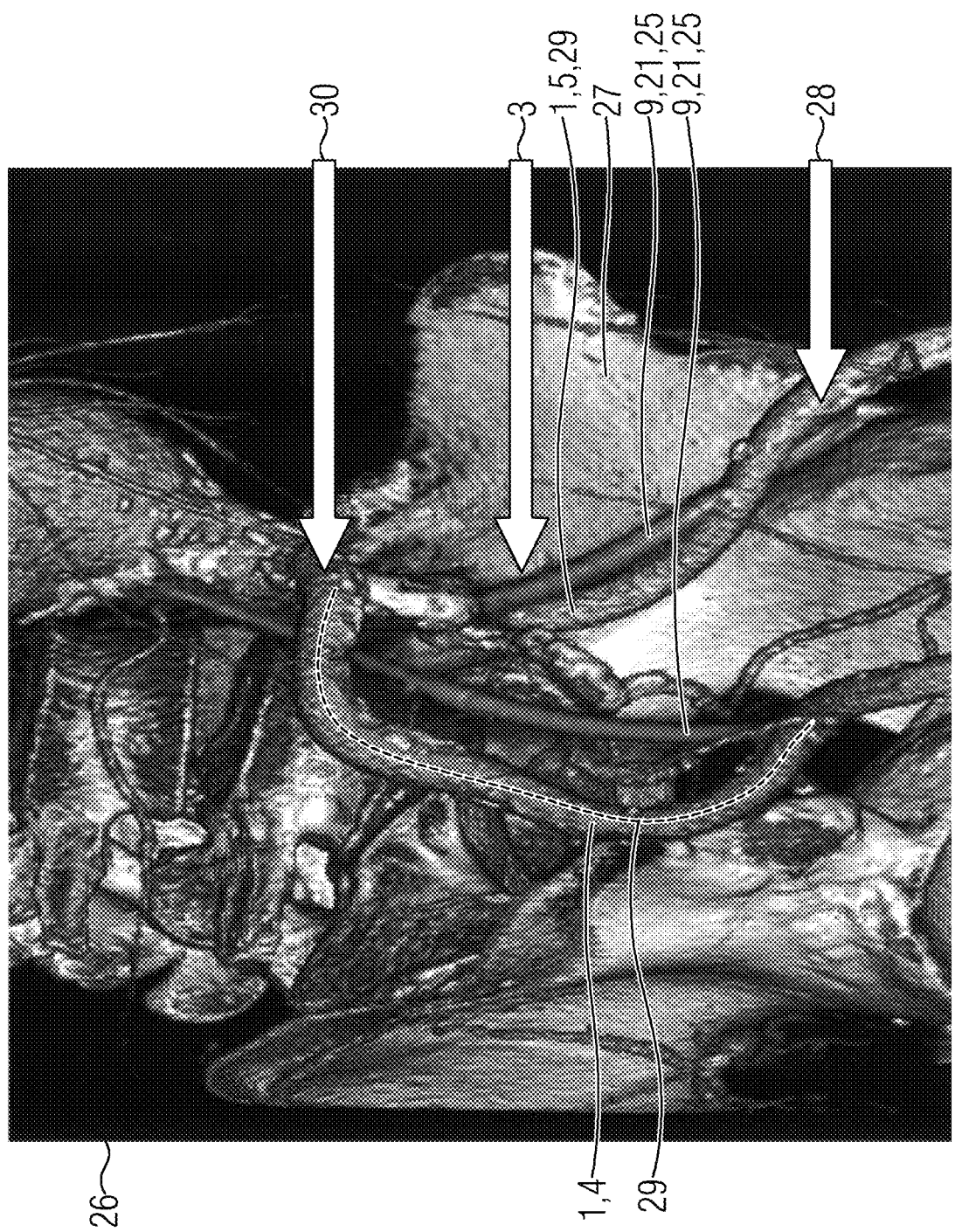
FIG. 6 depicts a superimposition diagram including an example of a pre-operative 3D CT image dataset and an intraoperatively recorded 2D CT image.

On the basis of the 2D superimposition image 21 shown in FIG. 5 and/or on the basis of the 3D superimposition image 26 shown in FIG. 6, for example, in a method act S9, an accuracy of the deformation correction or of the corresponding simulation or modeling of the deformation of the hollow organ 1 or of the undeformed model 23 may be determined or checked. For example, it may be seen in the 2D superimposition image 21 that in the deformed model 25 the anatomical feature 24 is consistent with the contrast medium shadow 22, e.g., is evidently arranged realistically, while this is not the case with the undeformed model 23, e.g., in FIG. 4. Thus, if a distance between the anatomical feature 24 on the deformed model 25 and the same anatomical feature in the two-dimensional image is less than a predetermined distance threshold value, then it may be assumed that the simulation or modeling of the deformation of the undeformed model 23 has been carried out correctly, e.g., realistically. A doctor undertaking the treatment may thus continue with the procedure on the basis of the deformed model 25.

In a method act S10, areas of relatively great and/or relatively low compression and/or stretching of the hollow organ 1 or of the deformed model 25 may be determined. For example, areas of higher or greater compression or stretching may be areas or sections of the deformed model 25 in which the deformed or shifted, e.g., transformed, mesh elements, for example, mesh vertices, are at a smaller or greater distance from one another than in the undeformed model 23. Because after release of the stent 8 the guide facility 9 is removed again from the hollow organ 1, the organ will largely go back into its initial position, e.g., at least assumes the uninfluenced course 29 again. It may thus be assumed that in areas of great change in length corresponding resetting forces will also act, which may lead to a relative displacement of the stent 8. There is provision here for estimating appropriate compression or stretching information for the deformed model 25 on the basis of the deformation of the undeformed model 23. The corresponding areas may then be marked or identified, e.g., color-coded.

Figure 7:
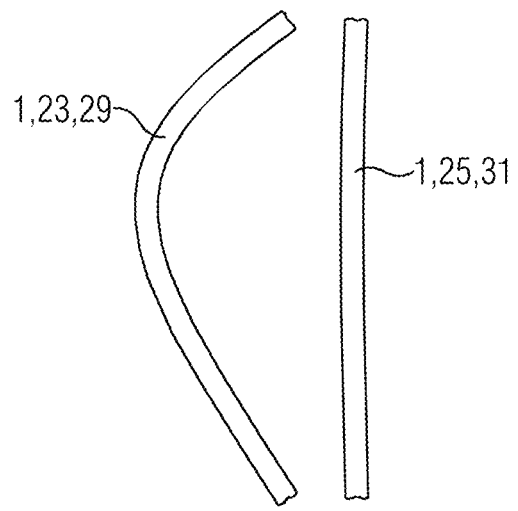
FIG. 7 depicts a schematic diagram of an example of an uninfluenced and a deformed course of a hollow organ.
Figure 8:
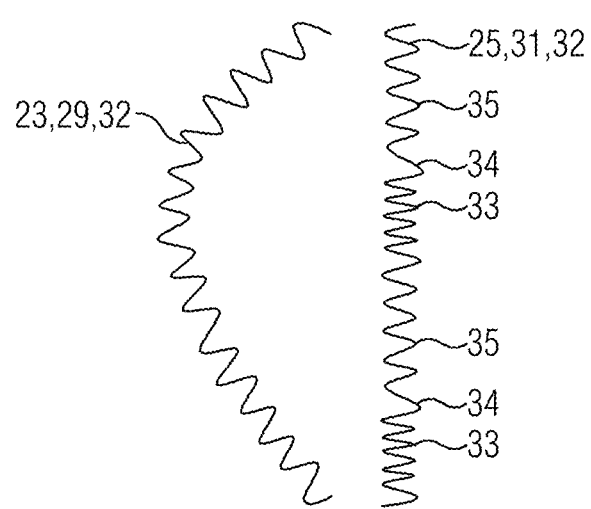
FIG. 8 depicts a schematic diagram for illustrating an example of an inhomogeneous change in length of the hollow organ from FIG. 7.
Figure 9:
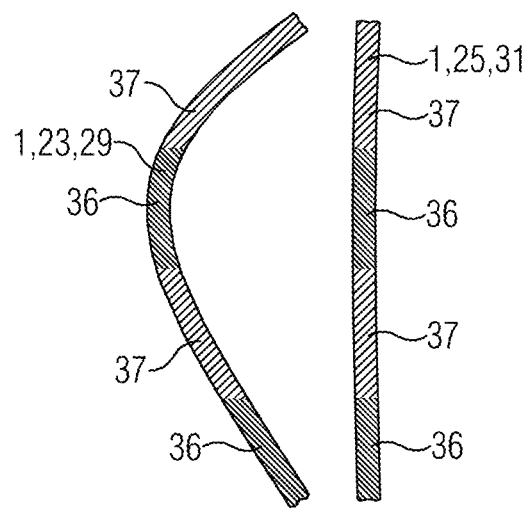
FIG. 9 depicts the schematic diagram from FIG. 7 with an example of identified areas of relatively great and relatively small change in length.

For simplified explanation, FIG. 7 depicts a schematic diagram of the hollow organ 1 in its undeformed, e.g., uninfluenced, course 29 and its deformed course 31. In the deformed course 31, the hollow organ 1 is shortened here compared to the uninfluenced course 29. This may likewise be reversed in other situations or application cases however, so that the hollow organ 1 may be stretched or lengthened during the deformation compared with its uninfluenced course 29. FIG. 8 depicts schematically how the hollow organ 1, for example, may be modeled as a spring 32. In the uninfluenced course 29, the spring 32 is at least homogeneous over its entire length, e.g., evenly loaded or stressed. In the deformed course 31, on the other hand, the spring 32 is loaded or stressed unevenly, e.g., inhomogeneously, e.g., compressed or stretched. Visibly shown here are compressed areas 33, stretched areas 34, and uncompressed areas 35. By comparison of a state of the spring 32 in the uninfluenced course 29 and in the deformed course 31, areas of relatively great or relatively low compression and/or stretching may thus be determined accordingly, which are produced in the deformation from the uninfluenced course 29 into the deformed course 31 and correspondingly in a reformation from the deformed course 31 into the uninfluenced course 29. Indicated or marked correspondingly schematically in FIG. 9 are relatively great changes in length 36 and relatively small changes in length 37 area-by-area, e.g., spatially resolved, both in the deformed course 31, also on the deformed model 25, and also in the uninfluenced course 29, also on the undeformed model 23. In this figure the changes in length 36, 37 may be determined on the basis of the deformed course 31, e.g., on the basis of the deformed model 25 and then transferred by assignment to the uninfluenced course 29, e.g., the undeformed model 23. Likewise, however the reformation of the hollow organ 1 of the deformed model 25 after removal of the guide facility 9 may be simulated separately, wherein an influence of the stent 8 then inserted may be considered.

Then, in a method act S11, areas of the hollow organ 1 suitable as the landing zones 10 may be determined, for example, suggested automatically. Likewise, an optimal length of the stent 8 may be determined and suggested here, (e.g., automatically or semi-automatically), possibly taking into consideration corresponding predetermined conditions.

The procedure may subsequently be carried out or completed, e.g., the stent 8 actually inserted into the hollow organ and positioned optimally in the hollow organ 1 in accordance with the landing zone 10 determined.

In summary, with a procedure of this type, the objective is thus to place the landing zone 10 of a vascular prosthesis, here for example the stent 8, as far as possible in a sound area of the vessel wall, but in doing so not to consider any important vessel branches, for example the branching-off vessels 6. The problem in such cases may be that, specifically in the heavily curved iliacal vessels, relatively strong deformations and changes in length, e.g., compression and/or stretching, may occur through the introduction of stiff instruments, such as for example of the guide facility 9. If these instruments are removed again after release of the vascular prosthesis, the corresponding vessel may expand or contact back again entirely or almost entirely to an original length. These changes in length of the vessels may not be homogeneous. Vessel areas subjected to strong or great changes in length are however unsuitable as the landing zone 10 for the vascular prosthesis and are thus to be avoided, in order to avoid complications from a post-operative lengthening or shortening back to original lengths. Because such deformations are not able to be estimated on the basis of 2D angiographies or are only able to be estimated with difficulty, it is proposed here, on the basis of pre- and/or intra-operative data, to estimate areas in which for example a smallest or a greatest change in length occurs, in order to thus determine areas that are suitable or unsuitable respectively as the landing zone 10. This makes an improved planning of the procedure possible.

An advantage of this method lies in estimating, using a pre-operative simulation and/or an intra-operative detection of an introduced stiff wire or the like, here for example of the guide facility 9, the areas of a vessel, e.g., of the hollow organ 1, that are subject or will be subject to at least potentially relatively great changes in length. This then puts the doctor in a position, for a placement of the vascular prosthesis, for example of an iliacal stent, to select areas with the smallest possible change in length, in order in so doing to avoid a migration of the stent and/or other post-operative complications. In this case savings in contrast medium may advantageously also be made compared to conventional methods.

The method is not only able to be used in the way described here but in principle may be applied for all superimpositions of a segmentation.

Overall the examples described show how landing zones 10 with minimal changes in length may be determined, in order to give technical assistance that makes it possible for a doctor to carry out an interventional procedure for placing an auxiliary element in the hollow organ 1 without any complications.

Although the disclosure has been illustrated and described in greater detail by the exemplary embodiments, the disclosure is not restricted by the disclosed examples and other variations may be derived herefrom by the person skilled in the art without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for planning support for an interventional procedure for placing an auxiliary element in a hollow organ by a guide facility that is stiffer than the hollow organ, the method comprising:
   acquiring a three-dimensional (3D) image dataset that maps an uninfluenced course of the hollow organ;
   creating a model of the hollow organ in the uninfluenced course by segmentation of the 3D image dataset;
   simulating a deformation of the hollow organ based on a course of the guide facility in the hollow organ through a deformation of the model; and
   automatically determining and specifying a spatially resolved compression and/or stretching of the hollow organ in a direction of longitudinal extent in a deformed course in accordance with the deformed model compared to the uninfluenced course of the hollow organ, wherein the deformed course comprises a shortening or lengthening of the hollow organ in the direction of the longitudinal extent in comparison to the uninfluenced course of the hollow organ.

2. The method of claim 1, wherein at least an at least two-dimensional (2D) image, which maps the guide facility in the hollow organ, is recorded and is superimposed on the 3D image dataset, and
   wherein the course of the guide facility is determined from the at least two-dimensional image and/or the superimposition.

3. The method of claim 2, wherein an anatomical feature of the hollow organ is identified in the 3D image dataset,
   wherein the anatomical feature is also visible with an imaging modality used for the at least two-dimensional (2D) image and is at least likely to be displaced by an introduction of the guide facility,
   wherein the anatomical feature is identified in the at least 2D image,
   wherein the deformed model is superimposed on the at least 2D image, and
   wherein, to establish an accuracy of the simulation of the deformation in the superimposition, a distance between the anatomical feature is determined from the at least 2D image and a same anatomical feature on the deformed model.

4. The method of claim 1, wherein, to determine the course of the guide facility in the hollow organ, the course is estimated based on a location of a predetermined planned insertion point for feeding the guide facility into the hollow organ relative to a predetermined planned target region for the auxiliary element and based on a predetermined shape and stiffness of the guide facility before the guide facility is fed into the hollow organ.

5. The method of claim 1, wherein a surface of the hollow organ is emulated by virtual mesh elements to create the model of the hollow organ, and
   wherein the spatially resolved compression and/or stretching is determined by determination and comparison of a plurality of distances between mesh elements adjacent to each other before and after the deformation.

6. The method of claim 1, wherein the spatially resolved compression and/or stretching is determined by a finite element method (FEM) simulation on the model of the hollow organ.

7. The method of claim 1, wherein the simulation of the deformation of the hollow organ is carried out under a boundary condition of a minimal expenditure of energy.

8. The method of claim 1, wherein, before the simulation of the deformation, at least one fixed point is predetermined, and
   wherein the at least one fixed point remains in a fixed position during the simulation and the deformation.

9. The method of claim 8, wherein the at least one fixed point comprises an insertion point for feeding the guide facility into the hollow organ and/or a bifurcation of the hollow organ.

10. The method of claim 1, wherein, based on the 3D image dataset, an inhomogeneity that influences a flexibility of the hollow organ area-by-area is detected, and
    wherein, for an area of the model corresponding to the inhomogeneity, an increased stiffness value is predetermined for the simulation of the deformation compared to a remainder of the model.

11. The method of claim 10, wherein the inhomogeneity comprises a calcification.

12. The method of claim 1, wherein, to specify the spatially resolved compression and/or stretching related in each case to an extent of the compression and/or stretching of the hollow organ determined along the deformed model, at least one area on the deformed model and a corresponding area on the uninfluenced course is color coded in accordance with a predetermined color scale.

13. The method of claim 1, wherein a flexibility of the auxiliary element and/or an anchoring point of the auxiliary element at a fixed location on the hollow organ is predetermined on the hollow organ,
   wherein a discrete reformation of the hollow organ with inserted auxiliary element and without the guide facility is simulated as a function of the spatially resolved stretching and/or compression and of the flexibility of the auxiliary element and/or the anchoring point of the auxiliary element, and
   wherein, based on the discrete reformation simulation, a likely displacement of the auxiliary element in the hollow organ between its position before and after the reformation is determined.

14. The method of claim 1, wherein a part area of the hollow organ to be treated by the auxiliary element is predetermined, and
   wherein, depending on the spatially resolved compression and/or stretching, a length of the auxiliary element is suggested automatically.

15. An imaging device for planning support for an interventional procedure for placing an auxiliary element in a hollow organ by a guide facility that is stiffer than the hollow organ, the imaging device comprising:
   a processor configured to:
      receive a three-dimensional (3D) image dataset acquired by the imaging device, wherein the 3D image dataset maps an uninfluenced course of the hollow organ;
      create a model of the hollow organ in the uninfluenced course by segmentation of the 3D image dataset;
      simulate a deformation of the hollow organ based on a course of the guide facility in the hollow organ through a deformation of the model; and
      automatically determine and specify a spatially resolved compression and/or stretching of the hollow organ in a direction of longitudinal extent in a deformed course in accordance with the deformed model compared to the uninfluenced course of the hollow organ, wherein the deformed course comprises a shortening or lengthening of the hollow organ in the direction of the longitudinal extent in comparison to the uninfluenced course of the hollow organ.

16. A non-transitory computer-readable storage medium on which a computer program is stored, wherein the computer program, when executed by an imaging device, causes the imaging device to:
   acquire a three-dimensional (3D) image dataset that maps an uninfluenced course of a hollow organ;
   create a model of the hollow organ in the uninfluenced course by segmentation of the 3D image dataset;
   simulate a deformation of the hollow organ based on a course of a guide facility in the hollow organ through a deformation of the model; and
   automatically determine and specify a spatially resolved compression and/or stretching of the hollow organ in a direction of longitudinal extent in a deformed course in accordance with the deformed model compared to the uninfluenced course of the hollow organ, wherein the deformed course comprises a shortening or lengthening of the hollow organ in the direction of the longitudinal extent in comparison to the uninfluenced course of the hollow organ.

* * * * *